United States Patent [19]

Rogers

[11] Patent Number: 5,569,229
[45] Date of Patent: Oct. 29, 1996

[54] VIEW FLAP DIAPER

[75] Inventor: Candies M. Rogers, 16031 Tacoma, Detroit, Mich. 48205

[73] Assignees: Candies M. Rogers, Detroit, Mich.; Peter D. Keefe, Roseville, Mich.

[21] Appl. No.: 332,245

[22] Filed: Oct. 31, 1994

[51] Int. Cl.$^6$ .................................................. A61F 13/15
[52] U.S. Cl. ........................ 604/385.1; 604/358; 604/395
[58] Field of Search ............................... 604/385.1, 358, 604/361, 385.2, 393–395

[56] References Cited

U.S. PATENT DOCUMENTS

| | | | |
|---|---|---|---|
| 3,604,423 | 9/1971 | Fraser | 604/385.1 |
| 3,901,237 | 8/1975 | Cepuritis et al. | 604/390 |
| 3,918,454 | 11/1975 | Korodi et al. | 604/361 |
| 3,952,746 | 4/1976 | Summers | 604/361 |
| 4,507,121 | 3/1985 | Leung | 604/361 |
| 4,704,116 | 11/1987 | Enloe . | |
| 4,704,117 | 11/1987 | Mitchell . | |
| 4,753,645 | 6/1988 | Johnson . | |
| 4,753,646 | 6/1988 | Enloe . | |
| 4,753,647 | 6/1988 | Curtis . | |
| 4,753,649 | 6/1988 | Pazdernik . | |
| 4,798,603 | 1/1989 | Meyer et al. . | |
| 4,931,051 | 6/1990 | Castello | 604/361 |
| 5,078,708 | 1/1992 | Haque | 604/361 |
| 5,207,663 | 5/1993 | McQueen | 604/358 |

FOREIGN PATENT DOCUMENTS 2042342  9/1980  United Kingdom ................ 604/385.1

OTHER PUBLICATIONS

Copy of Packaging for Huggies(TM) Supertrim Disposable Diapers Of Kimberly–Clark Corp., Neenah, WI 54957, Dated 1978.

*Primary Examiner*—John G. Weiss
*Assistant Examiner*—Mark O. Polutta
*Attorney, Agent, or Firm*—Peter D. Keefe

[57] ABSTRACT

A diaper equipped with a view flap that allows a guardian to determine whether or not the diaper needs changing with a minimum of intrusion and bother, in that partial disrobing of the diaper is obviated. The view flap diaper according to the present invention is composed of a diaper member having an aperture and a view flap member wherein the view flap member is selectively openable and closable with respect to the aperture of the diaper member. A liquid absorbent inner layer bonded with a liquid impermeable outer layer is the preferred diaper structure. The inner layer may include a liquid permeable liner, and may not have areas of differing absorbency.

17 Claims, 1 Drawing Sheet

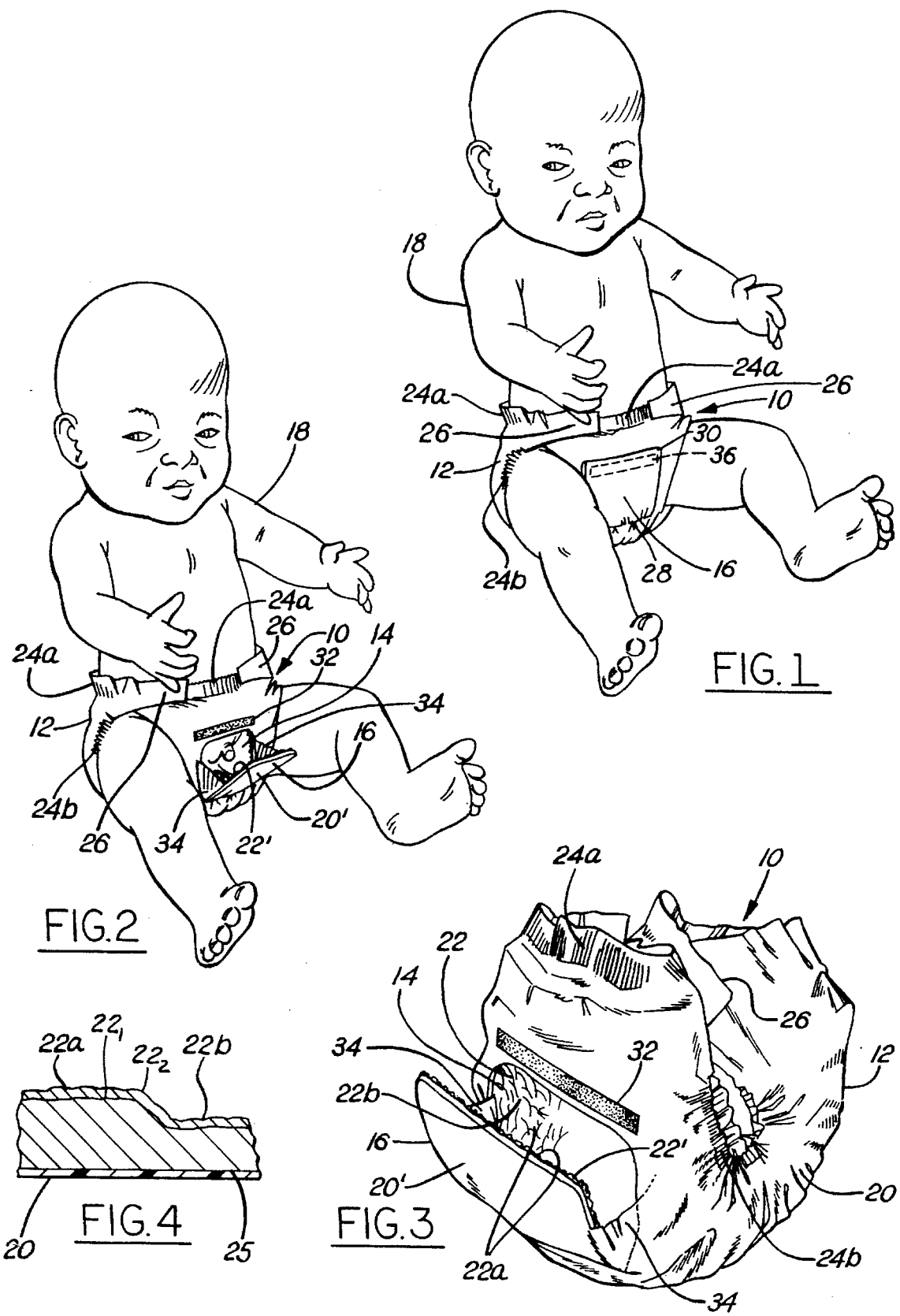

VIEW FLAP DIAPER

BACKGROUND OF THE INVENTION

1. Field of the invention

The present invention relates to diapers, particularly, but not exclusively, to disposable diapers having a plastic outer layer and an absorbent inner layer. Still more particularly, the present invention relates to a diaper having a view flap which is selectively openable and closable with respect thereto, wherein a guardian of a baby may easily examine whether or not the diaper needs changing without the bother of having to partly remove the diaper from the baby to make such an examination.

2. Description of the Prior Art

Diapers have long been the under garment of choice for babies because they serve to retain the liquid and solid excrement from the baby. Diaper technology has evolved over the years, having gone beyond simple cloth diapers to multicomponent disposable diapers having advanced body contour hugging and liquid absorbing features, such as for example described in U.S. Pat. Nos. 4,753,646; 4,753,647; 4,753,649; 4,704,116; and 4,704,117.

While it is the case that diaper technology has advanced, it is still a problem for the baby's guardian to inspect the inside of the diaper to see if the baby has done his or her business and whether or not changing of the diaper is warranted. To do this, the guardian must at least partly release the diaper from the baby, pull the diaper away from the baby sufficiently to get a good view, and then either remove the diaper completely if changing is warranted or reattach the diaper if changing is not warranted. While this procedure is troublesome for the guardian to perform, the baby may find this intrusion to be quite disturbing and thereupon set-off a crying episode.

Accordingly, it would be beneficial if somehow a guardian could inspect a baby to see if the diaper needs changing without having to partly disrobe the diaper from the baby.

SUMMARY OF THE INVENTION

The present invention is a diaper that allows a guardian to determine whether or not the diaper needs changing with a minimum of intrusion and bother, in that partial disrobing of the diaper is obviated. The view flap diaper according to the present invention is composed of a diaper member and a view flap member wherein the view flap member is selectively openable and closable with respect to the diaper member.

In the preferred embodiment, the view flap diaper according to the present invention is composed of a diaper member in the form of a disposable diaper having a plastic outer layer and an absorbent inner layer, and further composed of a view flap member connected with the diaper member. The plastic outer layer is preferably very thin, flexible and liquid impermeable. The absorbent inner layer preferably is composed of a soft and highly absorbent material and a liquid permeable liner. Preferably, the diaper member is form fitted to closely contour with respect to a baby's anatomy and has elastic gathers to enhance the fit of the diaper member with respect to the baby. The diaper member has an aperture formed therein. The view flap member is structured similarly to that of the diaper member, in that it is composed of a plastic outer layer and an absorbent inner layer similarly constructed to that of the diaper member, and is dimensioned so as to close the aperture. The view flap member is connected with the diaper member at a first end thereof. A second end of the view flap member opposite the first end is releasably connectable to the diaper member to thereby selectively hold the view flap member closed with respect to the aperture. Preferably, a flexible web is formed at each side of the first end and the diaper member to thereby provide assurance that excrement from the baby remains trapped in the view flap diaper when the view flap member is opened. Preferably, the view flap member is positioned with respect to the diaper member so that the view flap member is located in front of the baby, as this location provides the guardian with easily obtained information about whether liquid and/or solid excrement is present.

These, and additional objects, advantages, features and benefits of the present invention will become apparent from the following specification.

BRIEF DESCRIPTION OF THE DRAWINGS

FIG. 1 is a perspective view of a view flap diaper according to the present invention shown in operation with respect to a baby, wherein the view flap is shown in a closed position.

FIG. 2 is a perspective view of a view flap diaper according to the present invention shown in operation with respect to a baby, wherein the view flap is shown in an open position.

FIG. 3 is a perspective view of a view flap diaper according to the present invention.

FIG. 4 is a detail sectional edge view of the diaper member of the view flap diaper, showing an example absorbency areas provided by areas of differing thickness.

DETAILED DESCRIPTION OF THE PREFERRED EMBODIMENT

Referring now to the Drawing, it will be seen by reference to FIGS. 1 and 2 that the view flap diaper 10 according to the present invention is composed of a diaper member 12 having and aperture 14 and a view flap member 16 which is located at the aperture and which serves as a selective covering for the aperture. The preferred location for the aperture 14 is such as to locate it at the front of the baby 18, as this provides easy viewing by a guardian as to whether either solid or liquid excrement is present within the view flap diaper 10, and if so whether changing of the diaper is warranted. Alternatively, the aperture 14 could be located elsewhere, such as behind the baby 18, but this would likely make ascertaining whether or not either one or both of liquid and solid waste are present in the view flap diaper 10 a little more difficult for the guardian.

The diaper member 12 is preferred to be of the type known in the art as a disposable diaper having a liquid impermeable outer layer 20, such as a thin and flexible plastic layer, and an extremely liquid absorbent inner layer 22 that is connected to the outer layer such as by sonic or adhesive bonding (see FIG. 3). Preferably, the inner layer 22 is composed of a highly liquid absorbent material $22_1$ and a liquid permeable liner $22_2$ bonded thereto (see FIG. 4). An acceptable diaper construction is described by way of example in U.S. Pat. No. 4,753,649 to Pazdernik, dated Jun. 28, 1988, which diaper construction teaching is hereby incorporated by reference. The inner and outer layers 20, 22 provide a synergistic result which provides the baby with comfort while also protecting the baby's outer clothes and other immediate surroundings of the baby from excrement contact. Still further in this regard, the diaper member 12 is provided with a predetermined shape for conforming to the anatomy of a baby, for example as this pertains to the waist and legs. Preferably, elastic gathers are provided which air in form fit conformance of the diaper member with respect to the anatomical parts of the baby, such as by waist gathers 24a and legs gathers 24b. In order that the diaper member 12 be wrappingly fitted about the groin area of the baby 18, the outer layer 20 includes a pair of tabs 26 having a reusable and releasable type adhesive thereupon which allow the tabs to adhere to an adjoining portion of the waist area of the diaper member.

The inner layer 22 is preferably composed of areas having varying levels of absorbency based upon urination patterns that are uniquely produced by baby boys and by baby girls. For example as shown in FIG. 3, an area 22a is highly liquid absorbent, whereas an area 22b is not so highly absorbent, FIG. 4 shows an example of how the areas of differing absorbency may be achieved by providing at least two areas having differing thicknesses of the inner layer. Alternative structures can provide areas of differing absorbency, such as by areas of differing composition of the inner layer material wherein the level of absorbency differs with the differing compositions, or such as by providing areas of differing density of the absorbent material of the inner layer. Areas of differing absorbency are selected within a predetermined range of absorbency wherein the proper absorbency characteristics needed in the areas most critical to leakage and skin irritation are provided, yet also provided is minimized material in areas having less criticality to thereby minimize material cost and disposal problems.

Other alternative diaper member structures can be substituted for the above preferred embodiment of the diaper member 12, as the foregoing description is to be understood as being merely exemplary.

The view flap member 16 is located adjacent the aperture 14 and is sized to cover the aperture. A lower end 28 of the view flap member 16 is connected with the diaper member 12. In this regard, it is preferred for the view flap member 16 to be structured similarly to the diaper member 12, wherein the view flap member has a plastic outer layer 20' and an absorbent inner layer 22' having the aforementioned structural features of the inner layer 22 of the diaper member. The connection at the lower end 28 may be by integral connection to the diaper member 12 (at the outer layers and/or the inner layers thereof), by sewing to the diaper member, or by another attachment methodology known in the art, such as an adhesive.

In order that the view flap member 16 be selectively coverable over the aperture 14, the upper end 30 of the view flap member, located opposite the lower end 28, is structured for being releasably connected to the diaper member 12 adjacent the aperture 14. An example of a releasable connection is shown in FIGS. 1 through 3, wherein an adhesive strip 32 is provided on the diaper member adjacent the aperture 14 which is located such as to abut another adhesive strip connected with the view flap member adjacent the upper end thereof. Alternatively, one or the other of the view flap member 16 and the diaper member 12 may alone have an adhesive strip. Preferably in this regard, the adhesive strip 32 adheringly abuts to an adhesively releasable surface 36 connected with the inner layer 22' (the connection preferably being with respect to the aforementioned liner 22₂ of the inner layer) of the view flap member 16 so that a number of sealings and resealings may occur without loss of integrity of the connection of the upper end with respect to the diaper member adjacent the aperture. Of course, either the view flap member 16 or the diaper member 12 may be provided with the adhesively releasable strip, as is appropriate per the location of the adhesive strip. A releasable connection may be provided by other than adhesive, such as by VELCRO (trademark of Velcro, USA).

In order that any excrement contained in the view flap diaper 10 be retained therein during inspection through the aperture 14, it is preferred for the view flap member 16 adjacent the lower end 28 thereof and for the diaper member 12 adjacent thereto to be sealingly bridged by a flexible web 34. For example, the flexible web 34 may be formed of the liquid impermeable material of the outer layers 20, 20' and may be integrally or otherwise sealingly connected thereto.

In operation, the guardian places the diaper member of the view flap diaper upon the baby in the customary manner of present art diapers. Preferably, the aperture and its associated view flap member are located at the front groin area of the baby. The view flap diaper will now serve in the capacity of a diaper, absorbing and preventing loss of waste from the baby, inclusive of the diaper member and the view flap member.

When a guardian wishes to inspect whether or not the view flap diaper needs changing, the guardian simply grasps a portion of the view flap member adjacent the upper end thereof and thereupon causes the upper end of the view flap member to be released from the diaper member. The guardian then bends the view flap member, and/or otherwise pivots the view flap member at the connection of the view flap member to the diaper member at its lower end, to thereby see inside the diaper member through the aperture. If changing is warranted, the guardian thereupon changes the view flap diaper, if changing is not warranted, the guardian thereupon then causes the view flap member to be reattached at the upper end thereof by simply reconnecting together the releasable connection. This inspection process may be repeated a number of other times, and during each inspection, both the guardian and the baby are subjected to little or no bother or discomfort.

It is to be understood, that other forms of diapers other than disposable diapers may be equipped with a view flap member, such as for example conventional cloth diapers. Any such diaper equipped with a view flap member would include a diaper member having an aperture therein, a view flap member for selectively covering the aperture, a connection of the view flap member to the diaper member, and a releasable connection with respect to the view flap member and the diaper member as generally described hereinabove. Also, the aforementioned areas of differing absorbency of the inner layer may be provided on diapers with or without a view flap member.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A diaper equipped with a view flap, comprising:
    a diaper member having an aperture therein, said aperture having a predetermined shape and size so that a person is able to view therethrough into said diaper member and thereupon directly inspect for urinal and fecal excrement present in said diaper member;
    a view flap member having a lower end and an upper end, said lower end of said view flap member being connected with said diaper member adjacent said aperture, said view flap member being selectively movable from a closed position with respect to said aperture to an open position with respect to said aperture, wherein when said view flap member is in said open position the person is able to view through said aperture into said diaper member and thereupon directly inspect for presence of urinal and fecal excrement therein, said view flap member having a second predetermined shape and size wherein said view flap member covers and closes said aperture when said view flap member is in said closed position so that excrement is retained within said diaper member; and releasable connection means for releasably connecting said upper end of said view flap member to said diaper member adjacent said aperture.

2. The diaper of claim 1, wherein a pair of flexible webs sealingly join said view flap member to said diaper member adjacent said lower end of said view flap member.

3. The diaper of claim 2, wherein said inner layer of said diaper member comprises at least two selected absorbent areas having respectively differing absorbency greater than zero, further wherein the area having greater absorbency is at least located whereat a wearer of said diaper who has a preselected gender urinates.

4. The diaper of claim 1, wherein said inner layer of said diaper member comprises at least two selected absorbent areas having respectively differing absorbency greater than zero, further wherein the area having greater absorbency is at least located whereat a wearer of said diaper who has a preselected gender urinates.

5. The diaper of claim 1, wherein said diaper member comprises:

a liquid impermeable outer layer; and a liquid absorbent inner layer, said inner layer of said diaper member being bonded to said outer layer of said diaper member.

6. The diaper of claim 5, wherein said view flap member comprises:

a liquid impermeable outer layer; and a liquid absorbent inner layer, said inner layer of said view flap member being bonded to said outer layer of said view flap member;

wherein said outer layer of said diaper member is structurally similar to and interfaces with said outer layer of said view flap member so that when said view flap member is in said closed position said aperture is closed and excrement is retained in said diaper member by each of said outer layers, and wherein said inner layer of said diaper member is structurally similar to and interfaces with said inner layer of said view flap member so that when said view flap member is in said closed position excrement is absorbable by each of said inner layers.

7. The diaper of claim 6, wherein a pair of flexible webs sealingly join said outer layer of said view flap member to said outer layer of said diaper member adjacent said lower end of said view flap member.

8. The diaper of claim 7, wherein said inner layer of said diaper member comprises at least two selected absorbent areas having respectively differing absorbency greater than zero, further wherein the area having greater absorbency is at least located whereat a wearer of said diaper who has a preselected gender urinates.

9. The diaper member of claim 8, wherein said releasable connection means comprises:

a strip of a reusable and releasable adhesive connected to at least one of said upper end of said view flap and said diaper member adjacent said aperture.

10. The diaper member of claim 9, wherein said inner layer of said view flap member at said upper end thereof is provided with at least one of a strip of a release surface and a strip of a releasable adhesive.

11. The diaper member of claim 1, wherein said releasable connection means comprises:

a strip of a reusable and releasable adhesive connected to at least one of said upper end of said view flap and said diaper member adjacent said aperture.

12. The diaper member of claim 11, wherein said inner layer of said view flap member at said upper end thereof is provided with at least one of a strip of a release surface and a strip of a releasable adhesive.

13. The diaper of claim 12, wherein a pair of flexible webs sealingly join said outer layer of said view flap member to said outer layer of said diaper member adjacent said lower end of said view flap member.

14. The diaper of claim 13, wherein said inner layer of said diaper member comprises at least two selected absorbent areas having respectively differing absorbency greater than zero, further wherein the area having greater absorbency is at least located whereat a wearer of said diaper who has a preselected gender urinates.

15. A diaper equipped with a view flap, comprising:

a diaper member having an aperture therein, said aperture having a predetermined shape and size so that a person may view therethrough into said diaper member, wherein said diaper member comprises:

a liquid impermeable outer layer; and a liquid absorbent inner layer, said inner layer of said diaper member being bonded to said outer layer of said diaper member;

a view flap member having a lower end and an upper end, said lower end of said view flap member being connected with said diaper member adjacent said aperture, said view flap member being selectively movable from a closed position with respect to said aperture to an open position with respect to said aperture, wherein when said view flap member is in said open position the person may view through said aperture into said diaper member, said view flap member having a second predetermined shape and size wherein said view flap member covers and closes said aperture when said view flap member is in said closed position so that excrement is retained within said diaper member, wherein said view flap member comprises:

a liquid impermeable outer layer; and a liquid absorbent inner layer, said inner layer of said view flap member being bonded to said outer layer of said view flap member;

wherein said outer layer of said diaper member is structurally similar to and interfaces with said outer layer of said view flap member so that when said view flap member is in said closed position said aperture is closed and excrement is retained in said diaper member by each of said outer layers, and wherein said inner layer of said diaper member is structurally similar to and interfaces with said inner layer of said view flap member so that when said view flap member is in said closed position excrement is absorbable by each of said inner layers;

a pair of flexible webs sealingly joining said view flap member to said diaper member adjacent said lower end of said view flap member; and releasable connection means for releasably connecting said upper end of said view flap member to said diaper member adjacent said aperture.

16. The diaper of claim 14, wherein said inner layer of said diaper member comprises at least two selected absorbent areas having respectively differing absorbency greater than zero, further wherein the area having greater absorbency is at least located whereat a wearer of said diaper who has a preselected gender urinates.

17. A diaper member comprising:

a liquid impermeable outer layer; and a liquid absorbent inner layer, said inner layer of said diaper member being bonded to said outer layer of said diaper member;

wherein said inner layer of said diaper member comprises at least two selected absorbent areas having respectively differing absorbency greater than zero, further wherein the area having greater absorbency is at least located whereat a wearer of said diaper who has a preselected gender urinates, wherein said diaper member is provided with an aperture therein, said aperture having a predetermined shape and size so that a person may view therethrough into said diaper member; said diaper further comprising:

a view flap member having a lower end and an upper end, said lower end of said view flap member being connected with said diaper member adjacent said aperture, said view flap member being selectively movable from a closed position with respect to said aperture to an open position with respect to said aperture, wherein when said view flap member is in said open position the person may view through said aperture into said diaper member, said view flap member having a second predetermined shape and size wherein said view flap member covers and closes said aperture when said view flap member is in said closed position so that excrement is retained within said diaper member, wherein said view flap member comprises:

a liquid impermeable outer layer; and a liquid absorbent inner layer, said inner layer of said view flap member being bonded to said outer layer said view flap member;

wherein said outer layer of said diaper member is structurally similar to and interfaces with said outer layer of said view flap member so that when said view flap member is in said closed position said aperture is closed and excrement is retained in said diaper member by each of said outer layers, and wherein said inner layer of said diaper member is structurally similar to and interfaces with said inner layer of said view flap member so that when said view flap member is in said closed position excrement is absorbable by each of said inner layers;

a pair of flexible webs sealingly joining said view flap member to said diaper member adjacent said lower end of said view flap member; and releasable connection means for releasably connecting said upper end of said view flap member to said diaper member adjacent said aperture.

\* \* \* \* \*